(12) United States Patent
Liu

(10) Patent No.: US 10,507,096 B2
(45) Date of Patent: Dec. 17, 2019

(54) ARTIFICIAL BLOOD VESSEL AND PREPARATION METHOD THEREOF

(71) Applicant: Chang Liu, Beijing (CN)

(72) Inventor: Chang Liu, Beijing (CN)

( * ) Notice: Subject to any disclaimer, the term of this patent is extended or adjusted under 35 U.S.C. 154(b) by 286 days.

(21) Appl. No.: 15/662,402

(22) Filed: Jul. 28, 2017

(65) Prior Publication Data

US 2017/0325933 A1 Nov. 16, 2017

Related U.S. Application Data

(63) Continuation of application No. PCT/CN2015/079792, filed on May 26, 2015.

(30) Foreign Application Priority Data

Mar. 5, 2015 (CN) .......................... 2015 1 0097472

(51) Int. Cl.
*A61F 2/06* (2013.01)
*A61L 27/16* (2006.01)
(Continued)

(52) U.S. Cl.
CPC ................ *A61F 2/062* (2013.01); *A61F 2/06* (2013.01); *A61L 27/16* (2013.01); *A61L 27/18* (2013.01);
(Continued)

(58) Field of Classification Search
CPC .... A61F 2/062; A61F 2210/0076; A61F 2/06; A61F 2240/001; A61L 27/20;
(Continued)

(56) References Cited

U.S. PATENT DOCUMENTS 5,855,610 A * 1/1999 Vacanti ................... A61L 27/18
623/2.13
6,537,567 B1 * 3/2003 Niklason ............... A61L 27/507
424/422
(Continued)

FOREIGN PATENT DOCUMENTS

CN 1718172 A 1/2006
CN 101584612 A 11/2009
(Continued)

*Primary Examiner* — Navin Natnithithadha
*Assistant Examiner* — Sunita Reddy
(74) *Attorney, Agent, or Firm* — Erson IP (Nelson IP)

(57) ABSTRACT

The artificial blood vessel comprises a cortex layer, a fibroblast layer, a smooth muscle cell layer, an endothelial cell layer and an inner cavity. According to the artificial blood vessel, the endothelial layer, the smooth muscle cell layer, the fibroblast layer and the cortex layer are orderly arranged in a three-dimensional space by utilizing integrated technologies of plasma spraying, electrospraying, electrospining, intra-mold pouring and 3D printing; anticoagulant activity of the artificial blood vessel is enhanced by adopting an anticoagulation factor; step-by-step induced differentiation of stem cells in the artificial blood vessel is realized by adopting a growth factor controlled release method; and the artificial blood vessel is cultured by a pulsatile reactor, so that the artificial blood vessel structurally and functionally simulates natural animal blood vessels and provides a corresponding substitute for vascular transplantation and repair.

6 Claims, 2 Drawing Sheets

(51) Int. Cl.
*A61L 27/22* (2006.01)
*A61L 27/18* (2006.01)
*A61L 27/24* (2006.01)
*A61L 27/38* (2006.01)
*A61L 27/50* (2006.01)
*A61L 27/20* (2006.01)
*A61L 27/36* (2006.01)
*A61L 27/44* (2006.01)

(52) U.S. Cl.
CPC ............. *A61L 27/20* (2013.01); *A61L 27/222* (2013.01); *A61L 27/225* (2013.01); *A61L 27/24* (2013.01); *A61L 27/3604* (2013.01); *A61L 27/3804* (2013.01); *A61L 27/3808* (2013.01); *A61L 27/3826* (2013.01); *A61L 27/3891* (2013.01); *A61L 27/44* (2013.01); *A61L 27/507* (2013.01); *A61F 2210/0076* (2013.01); *A61F 2240/001* (2013.01)

(58) Field of Classification Search
CPC ...... A61L 27/16; A61L 27/18; A61L 27/3891; A61L 27/3826; A61L 27/3808; A61L 27/3804; A61L 27/24; A61L 27/225; A61L 27/44; A61L 27/3604; A61L 27/222; A61L 27/507; C08L 5/04; C08L 23/06; C08L 23/12; C08L 67/04; C08L 69/00; C08L 75/04; C08L 5/08
USPC ............................................ 600/36; 435/395
See application file for complete search history.

(56) References Cited

U.S. PATENT DOCUMENTS

| | | | | |
|---|---|---|---|---|
| 6,642,243 | B1* | 11/2003 | Imanzahrai | A61K 31/137 514/165 |
| 8,143,055 | B2* | 3/2012 | Forgacs | A61L 27/222 435/325 |
| 8,192,348 | B2 | 6/2012 | Tranquillo | |
| 8,873,374 | B2 | 10/2014 | Davidson | |
| 2002/0188349 | A1* | 12/2002 | McAllister | A61F 2/06 623/1.41 |
| 2004/0237822 | A1* | 12/2004 | Boland | B01L 3/0268 101/483 |
| 2006/0240061 | A1* | 10/2006 | Atala | A61F 2/06 424/422 |
| 2006/0253192 | A1* | 11/2006 | Atala | A61F 2/2415 623/2.13 |
| 2006/0257447 | A1* | 11/2006 | Hinds | A61F 2/06 424/423 |
| 2007/0128171 | A1 | 6/2007 | Tranquillo | |
| 2009/0142307 | A1* | 6/2009 | Athanasiou | A61L 27/3817 424/93.7 |
| 2009/0275129 | A1* | 11/2009 | Cooper | A61L 27/18 435/366 |
| 2012/0095383 | A1* | 4/2012 | Radojicic | A61L 31/005 604/8 |
| 2012/0253456 | A1* | 10/2012 | Shin | C12N 5/0691 623/1.42 |
| 2013/0250751 | A1 | 9/2013 | Davidson | |
| 2013/0345794 | A1* | 12/2013 | Khatiwala | A61L 27/3808 623/1.35 |
| 2014/0050766 | A1* | 2/2014 | Levenberg | A61L 27/225 424/400 |

FOREIGN PATENT DOCUMENTS

| | | |
|---|---|---|
| CN | 103230309 A | 8/2013 |
| JP | 2003024351 A | 1/2003 |

\* cited by examiner

ARTIFICIAL BLOOD VESSEL AND PREPARATION METHOD THEREOF

CROSS-REFERENCE TO RELATED APPLICATIONS

This application is a continuation of International Patent Application No. PCT/CN2015/079792 with a filing date of May 26, 2015, designating the United States, now pending, and further claims priority to Chinese Patent Application NO. 201510097472.8 with a filing date of Mar. 5, 2015. The content of the aforementioned applications, including any intervening amendments thereto, are incorporated herein by reference.

FIELD OF THE INVENTION

The present invention relates to an artificial blood vessel and a preparation method thereof, and belongs to the technical fields of organ manufacture and biological materials.

BACKGROUND OF THE INVENTION

According to statistics of the World Health Organization, a cardiovascular disease is one of the diseases with the highest global incidence and death rate. Roughly more than 17 million people die from a heart disease in the world every year. The cardiovascular disease has become the biggest cause of death in European developed countries, at least 2 million people die from the cardiovascular disease every year, and the death rate accounts for about 40% of all deaths. The quantity of vascular grafts exceeds 1.4 million per year only in America. In China, with the increase of modern cardiovascular and cerebrovascular diseases, the lower-limb phlebocholosis incidence and coronary artery bypass surgeries are increased by years, and the quantity of operations in Beijing Fuwai Hospital only is about 1000 per year and is progressively increased at a speed of 20%. Morbidity of congenital heart disease is 6.7‰ in China. Tens of thousands of patients receive operations each year, and most of the patients need artificial blood vessels and valves with vascular tunnels. Clinical demands on artificial blood vessel grafts become increasingly prominent. Accompanying problems are preparation processes of artificial blood vessels and selection of the grafts. The clinical blood vessel grafts should generally have the following characteristics: (1) good blood compatibility and no thrombosis; (2) enough mechanical properties and suture resistant strength; (3) good biodegradability and tissue regeneration ability; (4) zero toxin and zero immunologic rejection in dissolved matters, exudates and degradation products; and (5) simple preparation method, wide material source and low price.

At present, clinical vasotransplantation is mainly in an autotransplantation manner or an allograft manner, and a donor source is greatly limited. Some blood vessel analogues can be prepared by utilizing tissue engineering or 3D printing technologies, but such products have severe defects in performance [Nerem R M, et al. Ann Rev Biomed Eng 2001; 3:225], such as poor suture resistant strength, acute and chronic embolism, intimal hyperplasia, aneurysm formation, susceptibility to infection, etc. A satisfied small-diameter vascular substitute is clinically absent [Bordenave L, et al. Clin Hemorheol Microcirc 2005; 33:227]. For example, professor Norotte, et al. in Columbia University in the City of New York have developed a biogel sphere 3D printing technology based on three-dimensional automatic computer assisted deposition for use in stentless small-diameter angioplasty, and only rapidness, repeatability, quantifiable property and other advantages of the angioplasty are reflected [Norotte C, et al. Biomaterials, 2009, 30: 5970]. Mironov V, et al. in Clemson University in America printed a layer of vascular endothelial cells on a host material layer by utilizing a refitted ink-jet printer to form a quasi-three-dimensional stereochemical structure similar to circle bread [Mironov V, et al. Trends Biotechnol., 2003; 21:157]. Only the characteristics of the ink-jet printer, such as high response speed, high forming precision, high forming speed, low forming material viscosity and the like, are reflected. Leong, et al. in Nanyang Technological University in Singapore manufactured a vascular scaffold structure by utilizing selective laser sintering (SLS) and research polymers suitable for the SLS technology and characteristics of formed structures thereof [Leong K F, et al. Biomaterials, 2003, 24: 2363], and the scaffold is a far from the artificial blood vessel. For another example, Skardal, et al. in the University of Utah in America printed a hyaluronic acid solution by utilizing an instrument purchased from Company Fab@home and cross-linked to prepare a vascular repair material by using tetrahedral polyethylene glycol tetraacrylate [Skardal A, et al. Biomaterials, 2010, 31: 6173]. Kasyanov, et al. in Medical University of South Carolina in America printed silica drops and tissue blocks by utilizing similar equipment Fab@CTI and simulate branch vessel parts in kidney [Kasyanov V, et al. Virtual and Physical Prototyping, 2011, 6(4): 197]. Wu, et al. in Urbana-Champaign of University of Illinois in America performed direct writing on organic paraffin by using self-made 3D printing equipment and soaked the paraffin with epoxy resin to form a vascular network structure which has branched structures and through which liquid can flow in and out [Wu W, et al. Soft Matter, 2010, 6: 739]. Miller, et al. in University of Pennsylvania in America printed carbohydrate glass into a latticed template first and compounded a cell-loaded solution by using a casting process to form a duct-like blood access [Miller J S, et al. Nature Materials, 2012, 11: 768]. Zhang, et al. in University of Washington in America formed an endothelial microfluidic channel in a natural collagen matrix by using similar lithography [Zhang Y, et al. PNAS, 2012, 109(24): 9342]. The products above reflect some characteristics of natural blood vessels from different points of view, but cannot meet transplantation and replacement requirements of the artificial blood vessel in aspects such as anticoagulant activity, suture resistance and growth repair capability. The anticoagulant activity, suture resistance and growth repair capability of materials are main barriers restricting clinical applications of various different artificial blood vessel repair materials and are also main directions of future development.

To construct an artificial blood vessel by utilizing a regenerative medicine principle has become a research hotspot in the existing medical and engineering fields. The existing engineering technologies, such as intra-mold pouring and three-dimensional printing technologies, cannot be used for preparing implantable artificial blood vessel repair materials which can be directly connected with human artery and vein vessels. These factors facilitate organic combination of various technologies. Various biological materials are realized by utilizing composite multi-nozzle 3D printing, electrospraying, intra-mold pouring, electrospining and other integrated technologies, and artificial blood vessel substitutes matched with structures and functions of natural blood vessels are prepared, thereby providing benefits for a large number of patients.

SUMMARY OF THE INVENTION

The purpose of the present invention is to provide an artificial blood vessel and a preparation method thereof, so as to structurally and functionally simulate a natural blood vessel for direct transplantation and replacement of various artery and vein vessels to achieve the purpose of repair and regeneration.

A technical solution of the present invention is as follows:

An artificial blood vessel sequentially comprises a cortex layer, a fibroblast layer, a smooth muscle cell layer, an endothelial cell layer and an inner cavity from outside to inside, wherein the cortex layer is formed by spraying a synthetic polymer solution through plasma spraying, electrospraying or electrospining technologies; the fibroblast layer, the smooth muscle cell layer and the endothelial cell layer are formed by infusing, through an intra-mold pouring technology or stacking, through a 3D printing technology a natural polymer solution containing cells; growth factors and anticoagulation factors with a mass percent of 0.01-1% are compounded in the natural polymer solution; and a diameter of the inner cavity is 0.1-8 mm.

In the artificial blood vessel in the present invention, a thickness of the endothelial cell layer is 0.001-0.2 mm; a thickness of the smooth muscle cell layer is 0.01-5 mm; and a thickness of the fibroblast layer is 0.001-0.2 mm.

In the above technical solution of the present invention, the natural polymer solution of the fibroblast layer, the smooth muscle cell layer and the endothelial cell layer adopts at least one of the following substances with a mass percent of 0.1-20%: gelatin, sodium alga acid, dextrose, collagens, fibrinogens, bioactive peptides, chitosan, hyaluronic acid, extracellular matrixes, gelose, laminin, chondroitin sulfate, carrageenan and protein polysaccharide solution; a solvent in the natural polymer solution is selected from a group consisting of phosphate buffer, cell culture fluid, normal saline, serum or body fluid; the synthetic polymer solution of the cortex layer adopts at least one of the following substances with a mass-volume percent of 0.1-30%: polyurethane, polyethylene, polypropylene, polyvinyl chloride, polycaprolactone, polycarbonate, polyethylene glycol, polylactide-glycolide acid, polyester and polyhydroxyalkanoates; and a solvent in the synthetic polymer solution is tetraethylene glycol or 1,4-dioxane.

Preferably, a cryopreservation factor with a mass percent of 1-10% is compounded in the natural polymer solution in the present invention, and density of cells in the natural polymer solution is $1\times10^{2-7}$ cells per mL.

In the present invention, cells contained in the natural polymer solution of the endothelial cell layer are endothelial cells or mixtures of stem cells and the endothelial cells or mixtures of the stem cells and endothelial cell growth factors; cells contained in the natural polymer solution of the smooth muscle cell layer are smooth muscle cells or mixtures of stem cells and the smooth muscle cells or mixtures of the stem cells and smooth muscle cell growth factors; cells contained in the natural polymer solution of the fibroblast layer are fibroblasts or mixtures of stem cells and the fibroblasts or mixtures of the stem cells and fibroblast growth factors; and the stem cells are selected from a group consisting of mesenchymal stem cells, bone marrow stem cells, umbilical cord blood stem cells, embryonic stem cells or induced pluripotent stem cells.

The present invention provides a preparation method for the artificial blood vessel, comprising the following steps:

a. preparing a natural polymer solution with a mass percent of 0.1-20% first, adding an anticoagulation factor with a mass percent of 0.01-1% into the natural polymer solution, and respectively adding endothelial cells, smooth muscle cells, fibroblasts, stem cells or mixtures of stem cells and growth factors into the natural polymer solution containing the anticoagulation factor, to prepare the natural polymer solution containing different cells, wherein a density of the cells in the natural polymer solution is $1\times10^{2-7}$ cells per mL;

b. preparing a series of hollow cylindrical molds of different diameters; sleeving a second hollow cylindrical mold with a larger diameter outside a first hollow cylindrical mold, wherein a gap is reserved between the two molds; infusing a natural polymer solution containing endothelial cells or mixtures of stem cells and the endothelial cells or mixtures of the stem cells and endothelial cell growth factors into the gap between the two molds by using a dropper or a syringe, and enabling natural polymers in the solution to crosslink or polymerize by utilizing a cross-linking agent or a polymerizing agent, to form an endothelial cell layer;

c. removing the second hollow cylindrical mold on the basis of the step 2); sleeving a third hollow cylindrical mold with a larger diameter outside the endothelial cell layer, wherein a gap is reserved in the middle; infusing a natural polymer solution containing smooth muscle cells or mixtures of the stem cells and the smooth muscle cells or mixtures of the stem cells and smooth muscle cell growth factors into the gap between the endothelial cell layer and the third hollow cylindrical mold by adopting the method in the step 2), and enabling the natural polymers in the solution to crosslink or polymerize by utilizing the cross-linking agent or the polymerizing agent, to form a smooth muscle cell layer;

d. removing the third hollow cylindrical mold on the basis of the step 3); sleeving a fourth hollow cylindrical mold with a larger diameter outside the smooth muscle cell layer, wherein a gap is reserved in the middle; infusing a natural polymer solution containing fibroblasts or mixtures of the stem cells and the fibroblasts or mixtures of the stem cells and fibroblast growth factors into the gap between the smooth muscle cell layer and the fourth hollow cylindrical mold by adopting the method in the step 2) or 3), and enabling the natural polymers in the solution to crosslink or polymerize by utilizing the cross-linking agent or the polymerizing agent, to form a fibroblast layer;

e. removing the first hollow cylindrical mold and the fourth hollow cylindrical mold, spraying a synthetic polymer solution layer with a mass-volume percent of 0.1-30% outside the fibroblast layer by utilizing plasma spraying, electrospraying or electrospining technologies, and extracting with an organic solvent to form a cortex layer; and f. putting an artificial blood vessel prepared in the step 5) into a culture box of a pulsatile bioreactor for performing pulsatile culture, enabling cell culture fluid to pass through the culture box; and sequentially adding the endothelial cell growth factors, the smooth muscle cell growth factors and the fibroblast growth factors into the cell culture fluid in the pulsatile culture process, so that the stem cells in the artificial blood vessel are sequentially transformed into the endothelial cells, the smooth muscle cells and the fibroblasts from inside to outside, and a pulsatile frequency is controlled to 1-100 times per minute.

The present invention provides another preparation method for the artificial blood vessel, comprising the following steps:

a. preparing a natural polymer solution with a mass percent of 0.1-20% first, adding an anticoagulation factor with a mass percent of 0.01-1% into the natural polymer solution, and respectively adding endothelial cells, smooth muscle cells, fibroblasts, stem cells or mixtures of stem cells and growth factors into the natural polymer solution containing the anticoagulation factor, to prepare the natural polymer solution containing different cells, wherein a density of the cells in the natural polymer solution is $1 \times 10^{2-7}$ cells per mL;

b. printing an endothelial cell layer, a smooth muscle cell layer and a fibroblast layer in a layer-by-layer manner from inside the outside by adopting a 3D printing technology, enabling natural polymers in the layers to crosslink or polymerize by utilizing a cross-linking agent or a polymerizing agent, and forming a hollow cylindrical three-dimensional structure, wherein the endothelial cell layer is a natural polymer solution containing endothelial cells or mixtures of stem cells and the endothelial cells or mixtures of the stem cells and endothelial cell growth factors; the smooth muscle cell layer is a natural polymer solution containing smooth muscle cells or mixtures of the stem cells and the smooth muscle cells or mixtures of the stem cells and smooth muscle cell growth factors; and the fibroblast layer is a natural polymer solution containing fibroblasts or mixtures of the stem cells and the fibroblasts or mixtures of the stem cells and fibroblast growth factors;

c. spraying a synthetic polymer solution layer with a mass-volume percent of 0.1-30% outside the fibroblast layer by utilizing plasma spraying, electrospraying or electrospining technologies, extracting with an organic solvent to form a cortex layer, and finally forming an artificial blood vessel with a three-dimensional structure; and d. putting the artificial blood vessel prepared in the step 3) into a culture box of a pulsatile bioreactor for performing pulsatile culture, enabling cell culture fluid to pass through the culture box; and sequentially adding the endothelial cell growth factors, the smooth muscle cell growth factors and the fibroblast growth factors into the cell culture fluid in the pulsatile culture process, so that the stem cells in the artificial blood vessel are sequentially transformed into the endothelial cells, the smooth muscle cells and the fibroblasts from inside to outside, and a pulsatile frequency is controlled to 1-100 times per minute.

Compared with the prior art, the present invention has the following advantages and outstanding effects that: (1) accurate spatial positioning of different cells and polymer materials is realized by utilizing integrated technologies such as intra-mold pouring, plasma spraying, electrospraying, electrospining or 3D printing and the like; structures and functions of human blood vessels can be simulated; and construction of the artificial blood vessel on a three-dimensional scale is realized; (2) cell and tissue structures in the artificial blood vessel are trained or cultured by a controllable three-dimensional stress field; the endothelial cells, the smooth muscle cells and the fibroblasts are arranged according to a certain direction to form different tissue areas; mechanical strength of the artificial blood vessel is improved, so that the artificial blood vessel has excellent anticoagulation, suture-resistant and regenerative functions while meeting demands of cell proliferation growth and metabolism; a change from the artificial blood vessel to the natural blood vessel is completed; and a purpose of repairing and regenerating human artery and vein vessels is achieved; and (3) the artificial blood vessel and the preparation method thereof are also applicable to other tubular tissues and organs, such as esophagus, trachea, fallopian tube, bile duct, urethra and bladder.

BRIEF DESCRIPTION OF THE DRAWINGS

In FIG. 1: 101—cortex layer; 102—fibroblast layer; 103—smooth muscle cell layer; 104—endothelial cell layer; and 105—inner cavity.

In FIG. 2: 1—culture bottle; 2—duct; 3, valve; 4—culture box; 5—piston compression mechanism; 6, control valve; 7—pulsating pump; 8—slide block; and 9—motor.

DETAILED DESCRIPTION OF THE EMBODIMENTS

The present invention is further described below in combination with drawings and embodiments.

Figure 1:
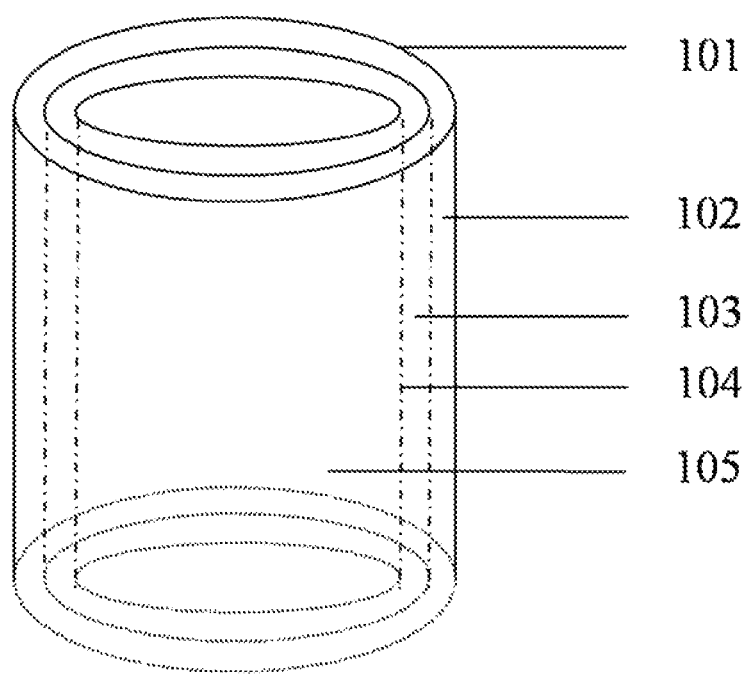
FIG. 1 is a three-dimensional structural schematic diagram of an artificial blood vessel.

FIG. 1 is a three-dimensional structural schematic diagram of an artificial blood vessel. The artificial blood vessel sequentially comprises a cortex layer 101, a fibroblast layer 102, a smooth muscle cell layer 103, an endothelial cell layer 104 and an inner cavity 105 from outside to inside, wherein the cortex layer 101 is formed by spraying a synthetic polymer solution through plasma spraying, electrospraying or electrospining technologies; the fibroblast layer 102, the smooth muscle cell layer 103 and the endothelial cell layer 104 are formed by infusing, through an intra-mold pouring technology or stacking, through a 3D printing technology a natural polymer solution containing cells; growth factors and anticoagulation factors with a mass percent of 0.01-1% are compounded in the natural polymer solution; and a diameter of the inner cavity 105 is 0.1-8 mm. A thickness of the endothelial cell layer is 0.001-0.2 mm; a thickness of the smooth muscle cell layer is 0.01-5 mm; and a thickness of the fibroblast layer is 0.001-0.2 mm.

The natural polymer solution of the fibroblast layer, the smooth muscle cell layer and the endothelial cell layer adopts at least one of the following substances with a mass percent of 0.1-20%: gelatin, sodium alga acid, dextrose, collagens, fibrinogens, bioactive peptides, chitosan, hyaluronic acid, extracellular matrixes, gelose, laminin, chondroitin sulfate, carrageenan and protein polysaccharide solution; a solvent in the natural polymer solution is at least one of phosphate buffer, cell culture fluid, normal saline, serum or body fluid; the synthetic polymer solution of the cortex layer adopts at least one of the following substances with a mass-volume percent of 0.1-30%: polyurethane, polyethylene, polypropylene, polyvinyl chloride, polycaprolactone, polycarbonate, polyethylene glycol, polylactide-glycolide acid, polyester and polyhydroxyalkanoates; and a solvent in the synthetic polymer solution is tetraethylene glycol or 1,4-dioxane.

A cryopreservation factor with a mass percent of 1-10% can also be compounded in the natural polymer solution which has a cell density of $1 \times 10^{2-7}$ cells per mL. Cells contained in the natural polymer solution of the endothelial cell layer are endothelial cells or mixtures of stem cells and the endothelial cells or mixtures of the stem cells and endothelial cell growth factors; cells contained in the natural polymer solution of the smooth muscle cell layer are smooth muscle cells or mixtures of stem cells and the smooth muscle cells or mixtures of the stem cells and smooth muscle cell growth factors; cells contained in the natural polymer solution of the fibroblast layer are fibroblasts or mixtures of stem cells and the fibroblasts or mixtures of the stem cells and fibroblast growth factors; and the stem cells are selected from a group consisting of mesenchymal stem cells, bone marrow stem cells, umbilical cord blood stem cells, embryonic stem cells or induced pluripotent stem cells.

The present invention provides a preparation method for the artificial blood vessel, comprising the following steps:

a. preparing a natural polymer solution with a mass percent of 0.1-20% first, adding an anticoagulation factor with a mass percent of 0.01-1% into the natural polymer solution, and respectively adding endothelial cells, smooth muscle cells, fibroblasts, stem cells or mixtures of stem cells and growth factors into the natural polymer solution containing the anticoagulation factor, to prepare the natural polymer solution containing different cells, wherein a density of the cells in the natural polymer solution is $1 \times 10^{2-7}$ cells per mL;

b. preparing a series of hollow cylindrical molds of different diameters; sleeving a second hollow cylindrical mold with a larger diameter outside a first hollow cylindrical mold, wherein a gap is reserved between the two molds; infusing a natural polymer solution containing endothelial cells or mixtures of stem cells and the endothelial cells or mixtures of the stem cells and endothelial cell growth factors into the gap between the two molds by using a dropper or a syringe, and enabling natural polymers in the solution to crosslink or polymerize by utilizing a cross-linking agent or a polymerizing agent, to form an endothelial cell layer;

c. removing the second hollow cylindrical mold on the basis of the step 2); sleeving a third hollow cylindrical mold with a larger diameter outside the endothelial cell layer, wherein a gap is reserved in the middle; infusing a natural polymer solution containing smooth muscle cells or mixtures of the stem cells and the smooth muscle cells or mixtures of the stem cells and smooth muscle cell growth factors into the gap between the endothelial cell layer and the third hollow cylindrical mold by adopting the method in the step 2), and enabling the natural polymers in the solution to crosslink or polymerize by utilizing the cross-linking agent or the polymerizing agent, to form a smooth muscle cell layer;

d. removing the third hollow cylindrical mold on the basis of the step 3); sleeving a fourth hollow cylindrical mold with a larger diameter outside the smooth muscle cell layer, wherein a gap is reserved in the middle; infusing a natural polymer solution containing fibroblasts or mixtures of the stem cells and the fibroblasts or mixtures of the stem cells and fibroblast growth factors into the gap between the smooth muscle cell layer and the fourth hollow cylindrical mold by adopting the method in the step 2) or 3), and enabling the natural polymers in the solution to crosslink or polymerize by utilizing the cross-linking agent or the polymerizing agent, to form a fibroblast layer;

e. removing the first hollow cylindrical mold and the fourth hollow cylindrical mold, spraying a synthetic polymer solution layer with a mass-volume percent of 0.1-30% outside the fibroblast layer by utilizing plasma spraying, electrospraying or electrospining technologies, and extracting with an organic solvent to form a cortex layer; and f. putting an artificial blood vessel prepared in the step 5) into a culture box of a pulsatile bioreactor for performing pulsatile culture; enabling cell culture fluid to pass through the culture box; and sequentially adding the endothelial cell growth factors, the smooth muscle cell growth factors and the fibroblast growth factors into the cell culture fluid in the pulsatile culture process, so that the stem cells in the artificial blood vessel are sequentially transformed into the endothelial cells, the smooth muscle cells and the fibroblasts from inside to outside, and a pulsatile frequency is controlled to 1-100 times per minute.

The present invention provides a second preparation method for the artificial blood vessel, comprising the following steps:

a. preparing a natural polymer solution with a mass percent of 0.1-20% first, adding an anticoagulation factor with a mass percent of 0.01-1% into the natural polymer solution, and respectively adding endothelial cells, smooth muscle cells, fibroblasts, stem cells or mixtures of stem cells and growth factors into the natural polymer solution containing the anticoagulation factor, to prepare the natural polymer solution containing different cells, wherein a density of the cells in the natural polymer solution is $1 \times 102-7$ cells per mL;

b. printing an endothelial cell layer, a smooth muscle cell layer and a fibroblast layer in a layer-by-layer manner from inside the outside by adopting a 3D printing technology, enabling natural polymers in the layers to crosslink or polymerize by utilizing a cross-linking agent or a polymerizing agent, and forming a hollow cylindrical three-dimensional structure, wherein the endothelial cell layer is a natural polymer solution containing endothelial cells or mixtures of stem cells and the endothelial cells or mixtures of the stem cells and endothelial cell growth factors; the smooth muscle cell layer is a natural polymer solution containing smooth muscle cells or mixtures of the stem cells and the smooth muscle cells or mixtures of the stem cells and smooth muscle cell growth factors; and the fibroblast layer is a natural polymer solution containing fibroblasts or mixtures of the stem cells and the fibroblasts or mixtures of the stem cells and fibroblast growth factors;

c. spraying a synthetic polymer solution layer with a mass-volume percent of 0.1-30% outside the fibroblast layer by utilizing plasma spraying, electrospraying or electrospining technologies, extracting with an organic solvent to form a cortex layer, and finally forming an artificial blood vessel with a three-dimensional structure; and d. putting the artificial blood vessel prepared in the step 3) into a culture box of a pulsatile bioreactor for performing pulsatile culture; enabling cell culture fluid to pass through the culture box; and sequentially adding the endothelial cell growth factors, the smooth muscle cell growth factors and the fibroblast growth factors into the cell culture fluid in the pulsatile culture process, so that the stem cells in the artificial blood vessel are sequentially transformed into the endothelial cells, the smooth muscle cells and the fibroblasts from inside to outside, and a pulsatile frequency is controlled to 1-100 times per minute.

Figure 2:
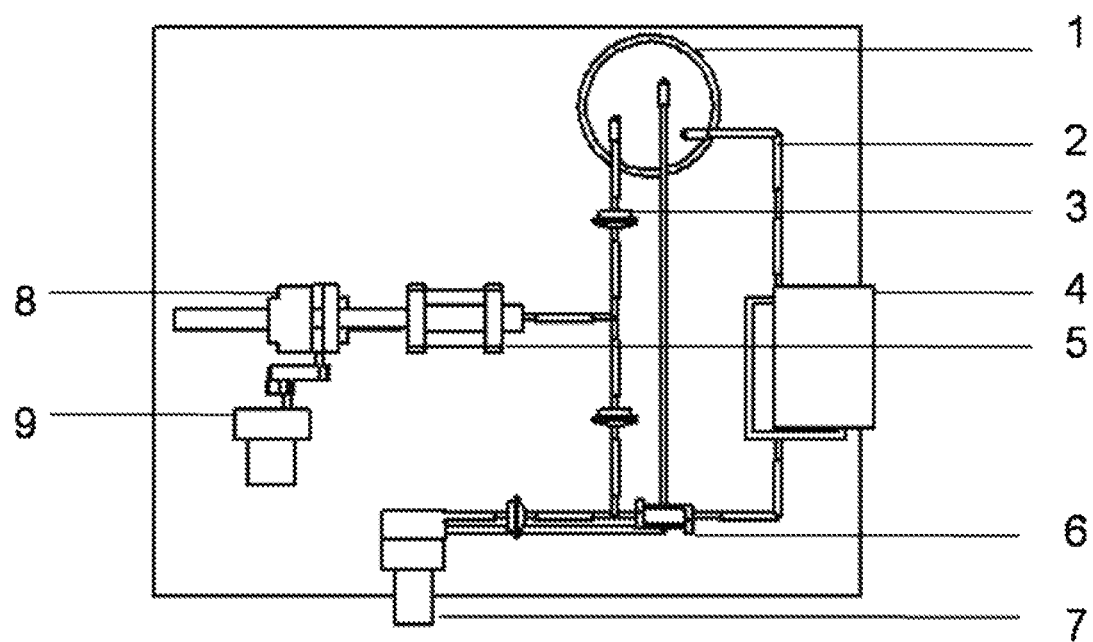
FIG. 2 is a structural schematic diagram of a pulsatile bioreactor.

FIG. 2 is a structural schematic diagram of a pulsatile bioreactor. The pulsatile bioreactor comprises a culture bottle 1, a duct 2, a valve 3, a culture box 4, a piston compression mechanism 5, a control valve 6, a pulsating pump 7, a slide block 8 and a motor 9, wherein the culture bottle, the culture box and the pulsating pump are connected by the duct; nutrient liquid passes through the culture box; and the artificial blood vessel is arranged in the culture box.

Embodiment 1: Small-Diameter Blood Vessel and Preparation Method Thereof

The preparation method comprises the following steps:

a. respectively preparing a sodium alga acid solution with a mass percent of 0.1% and a gelatin solution with a mass percent of 20%; uniformly mixing the sodium alga acid solution and the gelatin solution according to a volume ratio of 1:1, wherein 1% of an anticoagulation factor heparin and 10% of a cell cryopreservation factor dimethyl sulfoxide are added; and respectively mixing endothelial cells, smooth muscle cells and fibroblasts with the mixed solution, wherein a density of the cells in the sodium alga acid and gelatin mixed solution is $1\times10^2$ cells per mL;

b. loading various cell-containing solutions in the step a into a nozzle assembly of 3D printing equipment; printing a hollow cylinder of which an inner cavity has a diameter of 0.1 mm and which sequentially comprises an endothelial cell layer, a smooth muscle cell layer and a fibroblast layer from inside to outside in a layer-by-layer manner; and cross-linking sodium alga acid molecules by using a calcium chloride solution with a mass percent of 1%, to stabilize a three-dimensional structure;

c. spraying a polyethylene solution layer with a mass-volume percent of 30% outside the three-dimensional structure formed in the step b by utilizing a plasma spraying technology, and extracting with an organic solvent to form a cortex layer; and d. putting the artificial blood vessel prepared in the step c into a culture box of a pulsatile bioreactor, and performing pulsatile culture on the artificial blood vessel at a frequency of 100 times per minute by using culture solutions containing endothelial cell growth factors, smooth muscle cell growth factors and fibroblast growth factors respectively, to enhance connection strength and tensile strength among the cells.

Embodiment 2: Large-Diameter Blood Vessel and Preparation Method Thereof

The preparation method comprises the following steps:

a. preparing a series of hollow cylindrical molds with diameters more than 6 mm; respectively preparing fibrinogen solutions containing bone marrow stem cells, endothelial cells and fibroblasts, wherein the fibrinogen solution has a mass percent of 5% and density of the cells in the fibrinogen solution is $1\times10^7$ cells per mL; and respectively adding a smooth muscle cell growth factor with a mass percent of 1%, 1% of anticoagulation factor heparin and 10% of cell cryopreservation factor dimethyl sulfoxide into the bone marrow stem cell solution;

b. sleeving a second hollow cylindrical mold with a larger diameter outside a first hollow cylindrical mold with a smaller diameter, wherein a gap is reserved between the two molds; injecting the fibrinogen solution containing the endothelial cells and heparin into the gap between the two molds by using a dropper; and enabling fibrinogens in the solution to polymerize by utilizing thrombin with a mass percent of 10%, to form an endothelial cell layer;

c. removing the second hollow cylindrical mold on the basis of the step b; sleeving a third hollow cylindrical mold with a larger diameter outside the endothelial cell layer, wherein a gap is reserved in the middle; infusing the fibrinogen solution containing the bone marrow stem cells and heparin into the gap between the endothelial cell layer and the third hollow cylindrical mold by adopting the method in the step b; and enabling fibrinogens in the solution to polymerize by utilizing thrombin with a mass percent of 10%, to form a smooth muscle cell layer;

d. removing the third hollow cylindrical mold on the basis of the step c; sleeving a fourth hollow cylindrical mold with a larger diameter outside the smooth muscle cell layer, wherein a gap is reserved in the middle; infusing the fibrinogen solution containing the fibroblasts into the gap between the smooth muscle cell layer and the fourth hollow cylindrical mold by adopting the method in the step b or c; and enabling fibrinogens in the solution to polymerize by utilizing thrombin with a mass percent of 10%, to form a fibroblast layer;

e. removing the first hollow cylindrical mold and the fourth hollow cylindrical mold; spraying a polylactide-co-glycolide synthetic polymer solution layer with a mass percent of 0.1% outside the fibroblast layer by utilizing an electrospining technology, and extracting with an organic solvent to form a cortex layer; and f. putting the artificial blood vessel prepared in the step e into a culture box of a pulsatile bioreactor, and performing pulsatile culture at a frequency of once per minute by using culture solutions containing the endothelial cell growth factors, the smooth muscle cell growth factors and the fibroblast growth factors respectively, to enhance connection strength and tensile strength among the cells.

Embodiment 3: Medium-Diameter Blood Vessel and Preparation Method Thereof

The preparation method comprises the following steps:

a. preparing a series of hollow cylindrical molds with diameters of 2-6 mm; preparing collagen solutions containing adipose-derived stem cells, wherein the collagen solutions have a mass percent of 1% and a density of the adipose-derived stem cells in the collagen solution is $1\times10^5$ cells per mL; and respectively adding endothelial cell growth factors, smooth muscle cell growth factors and fibroblast growth factors with a mass percent of 0.01%, 0.01% of anticoagulation factor taxol and 1% of cell cryopreservation factor glycerin into the three solutions containing the adipose-derived stem cells;

b. sleeving a second hollow cylindrical mold with a larger diameter outside a first hollow cylindrical mold with a smaller diameter, wherein a gap is reserved between the two molds; injecting the collagen solution containing the adipose-derived stem cells, the endothelial cell growth factors, taxol and glycerin into the gap between the two molds by using a dropper; and enabling collagens in the solution to polymerize by utilizing sodium hydroxide with a mass percent of 1%, to form an endothelial cell layer;

c. removing the second hollow cylindrical mold on the basis of the step b; sleeving a third hollow cylindrical mold with a larger diameter outside the endothelial cell layer, wherein a gap is reserved in the middle; injecting the collagen solution containing the adipose-derived stem cells, the smooth muscle cell growth factors, taxol and glycerin into the gap between the endothelial cell layer and the third hollow cylindrical mold by adopting the method in the step b; and enabling collagens in the solution to polymerize by utilizing sodium hydroxide with the mass percent of 1%, to form a smooth muscle cell layer;

d. removing the third hollow cylindrical mold on the basis of the step c; sleeving a fourth hollow cylindrical mold with a larger diameter outside the smooth muscle cell layer, wherein a gap is reserved in the middle; injecting the collagen solution containing the adipose-derived stem cells, the fibroblast growth factors, taxol and glycerin into the gap between the smooth muscle cell layer and the fourth hollow cylindrical mold by adopting the method in the step b or c; and enabling collagens in the solution to polymerize by utilizing 1% of sodium hydroxide, to form a fibroblast layer;

e. removing the first hollow cylindrical mold and the fourth hollow cylindrical mold; spraying a polyurethane solution layer with a mass percent of 1% outside the fibroblast layer by utilizing an electrospining technology; and extracting with an organic solvent to form a cortex layer; and f. putting the artificial blood vessel prepared in the step e into a culture box of a pulsatile bioreactor, and performing pulsatile culture at a frequency of 80 times per minute by using culture solutions containing the endothelial cell growth factors, the smooth muscle cell growth factors and the fibroblast growth factors respectively, to enhance connection strength and tensile strength among the cells.

I claim:

1. An artificial blood vessel, sequentially comprising a cortex layer, a fibroblast layer, a smooth muscle cell layer, an endothelial cell layer and an inner cavity from outside to inside of the artificial blood vessel; wherein the cortex layer is formed by spraying a synthetic polymer solution through plasma spraying, electrospraying or electrospining technologies; the fibroblast layer, the smooth muscle cell layer and the endothelial cell layer are formed by infusing, through an intra-mold pouring technology or stacking, through a 3D printing technology a natural polymer solution containing cells; growth factors and anticoagulation factors with a mass percent of 0.01-1% are compounded in the natural polymer solution; and a diameter of the inner cavity is 0.1-8 mm.

2. The artificial blood vessel according to claim 1, wherein a thickness of the endothelial cell layer is 0.001-0.2 mm; a thickness of the smooth muscle cell layer is 0.01-5 mm; and a thickness of the fibroblast layer is 0.001-0.2 mm.

3. The artificial blood vessel according to claim 2, wherein the natural polymer solution of the fibroblast layer, the smooth muscle cell layer and the endothelial cell layer adopts at least one of the following substances with a mass percent of 0.1-20%: gelatin, sodium alga acid, dextrose, collagens, fibrinogens, bioactive peptides, chitosan, hyaluronic acid, extracellular matrixes, gelose, laminin, chondroitin sulfate, carrageenan and protein polysaccharide solution; a solvent in the natural polymer solution is selected from a group consisting of phosphate buffer, cell culture fluid, normal saline, serum or body fluid; the synthetic polymer solution of the cortex layer adopts at least one of the following substances with a mass-volume percent of 0.1-30%: polyurethane, polyethylene, polypropylene, polyvinyl chloride, polycaprolactone, polycarbonate, polyethylene glycol, polylactide-glycolide acid, polyester and polyhydroxyalkanoates; and a solvent in the synthetic polymer solution is tetraethylene glycol or 1,4-dioxane.

4. The artificial blood vessel according to claim 1, wherein the natural polymer solution of the fibroblast layer, the smooth muscle cell layer and the endothelial cell layer adopts at least one of the following substances with a mass percent of 0.1-20%: gelatin, sodium alga acid, dextrose, collagens, fibrinogens, bioactive peptides, chitosan, hyaluronic acid, extracellular matrixes, gelose, laminin, chondroitin sulfate, carrageenan and protein polysaccharide solution; a solvent in the natural polymer solution is selected from a group consisting of phosphate buffer, cell culture fluid, normal saline, serum or body fluid; the synthetic polymer solution of the cortex layer adopts at least one of the following substances with a mass-volume percent of 0.1-30%: polyurethane, polyethylene, polypropylene, polyvinyl chloride, polycaprolactone, polycarbonate, polyethylene glycol, polylactide-glycolide acid, polyester and polyhydroxyalkanoates; and a solvent in the synthetic polymer solution is tetraethylene glycol or 1,4-dioxane.

5. The artificial blood vessel according to claim 1, wherein a cryopreservation factor with a mass percent of 1-10% is compounded in the natural polymer solution, and a density of cells in the natural polymer solution is $1 \times 10^{2-7}$ cells per mL.

6. The artificial blood vessel according to claim 1, wherein cells contained in the natural polymer solution of the endothelial cell layer are endothelial cells or mixtures of stem cells and the endothelial cells or mixtures of the stem cells and endothelial cell growth factors; cells contained in the natural polymer solution of the smooth muscle cell layer are smooth muscle cells or mixtures of stem cells and the smooth muscle cells or mixtures of the stem cells and smooth muscle cell growth factors; cells contained in the natural polymer solution of the fibroblast layer are fibroblasts or mixtures of stem cells and the fibroblasts or mixtures of the stem cells and fibroblast growth factors; and the stem cells are selected from a group consisting of mesenchymal stem cells, bone marrow stem cells, umbilical cord blood stem cells, embryonic stem cells or induced pluripotent stem cells.

\* \* \* \* \*